United States Patent [19]

Buchanan et al.

[11] Patent Number: 5,122,613
[45] Date of Patent: Jun. 16, 1992

[54] FLUORINATED N,N-BIS-IMIDES

[75] Inventors: Robert A. Buchanan, Grand Island; Robert L. Ostrozynski, Williamsville; Henry C. Lin, Grand Island, all of N.Y.

[73] Assignee: Occidental Chemical Corporation, Niagara Falls, N.Y.

[21] Appl. No.: 708,319

[22] Filed: May 31, 1991

[51] Int. Cl.⁵ .................. C07D 209/56; C07D 207/04
[52] U.S. Cl. ...................... 548/435; 548/523
[58] Field of Search .................. 548/435, 523

[56] References Cited

FOREIGN PATENT DOCUMENTS 56-71067  6/1981  Japan ................ 548/435
63-264566 11/1988 Japan ................ 548/435

*Primary Examiner*—Mary C. Lee
*Assistant Examiner*—Joseph K. McKane
*Attorney, Agent, or Firm*—James F. Tao; Arthur S. Cookfair

[57] ABSTRACT

This invention relates to novel fluorinated N,N-bis-imides of the formula

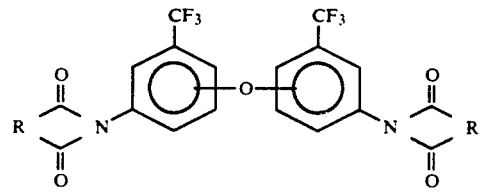

wherein R is a bivalent radical of the formula

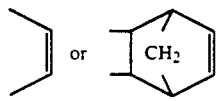

The compounds are particularly useful as monomers in the preparation of high performance polymer.

9 Claims, No Drawings

FLUORINATED N,N-BIS-IMIDES

BACKGROUND OF THE INVENTION

1. Field of the Invention

The present invention relates to novel fluorine-containing aromatic ether bis-imides, useful in the preparation of thermosetting resins.

2. Description of the Prior Art

Thermosetting resins having a structure based on imide linkages are used in industry for applications based on their advantageous properties, such as electrical insulation, thermal stability, and dimensional stability of molded articles. These addition-type polyimides are cross-linked polymers which may be prepared from bis-imides which are functionalized with unsaturated end groups, such as norbornenyl or ethynyl, capable of undergoing thermal polymerization to form a highly cross-linked polyimide. The polymers thus formed are thermoset and cannot be reprocessed by heat and pressure. Resins of this type are used in a variety of applications including, for example, impregnation varnish, molded articles or components, laminated boards, electronic circuit board manufacture, adhesives, etc. The importance of the various properties of the resin will vary depending on the end application for which it is intended, and the properties of a particular resin will depend, in part, on the elemental composition and structure of the bis-imide monomers employed. The fluorinated bis-imides of this invention are well-suited for use as monomers for the preparation of addition-type polyimides.

One important advantage of polyimides based on the fluorinated bismaleimides and bisnadimides of this invention is that of improved electrical properties. In particular, these polymers are useful as dielectric layers in microelectronic applications. The dielectric constant (measured by ASTM D 150-87) of a polyimide is the ratio of the capacitance of a capacitor containing the polyimide to the capacitance of the same electrode system with air replacing the insulation. Low dielectric values are preferred as this allows for increased circuit density and high speed-high frequency operation in the high megahertz region.

Another important property is moisture absorption which is a measure of the amount of moisture a polymer absorbs from the air at different humidities. Incorporation of fluorinated bismaleimides and bisnadimides of this invention lowers the moisture absorption of the polymer. A lower moisture absorption is important since the amount of moisture on a material has a strong effect on its electrical properties, such as the dielectric constant and the dissipation factor. In addition, a low moisture regain gives rise to other useful properties such as hydrolytic stability and greater resistance to caustic. This permits use of the polymers over a wider range of environmental conditions.

Another property of polymers incorporating the fluorinated monomers of this invention is high optical transparency. Polyimides incorporating these monomers are nearly transparent to slightly yellow in appearance and, as a result, are particularly useful for optical applications. Incorporation of fluorinated alkyl side chains in the backbone of the bis-imide moiety of these polyimides is responsible for increased optical transparency. Polyimides incorporating these monomers are less flammable due to the inclusion of the fluorinated bismaleimide and bisnadimide monomers of this invention.

Polyimides incorporating these fluorinated bisnadimide and bismaleimide monomers do not lose the usual useful properties typically associated with polyimides such as high thermal stability and excellent mechanical properties.

SUMMARY OF THE INVENTION

This invention relates to novel fluorine-containing aromatic ether bis-imides of the formula

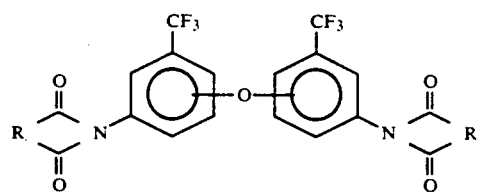

wherein R is a bivalent radical of the formula

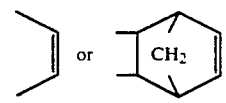

The compounds are particularly useful as monomers in the preparation of high performance polymer.

The bisimides of this invention (formula I) may be prepared by reacting a diamine of the formula

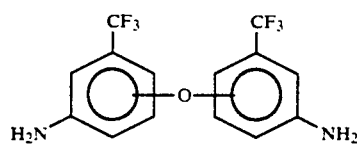

with 2 equivalents of an ethylenically unsaturated anhydride of the formula

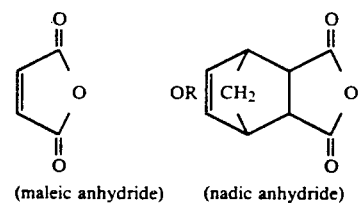

(maleic anhydride)     (nadic anhydride)

DETAILED DESCRIPTION OF THE INVENTION

The aromatic diamines (II) employed as starting materials in the preparation of the bisimides (I) of this invention may be conveniently prepared by (1) reaction, in the presence of water, of a selected nitro or halogen substituted nitrobenzotrifluoride with potassium fluoride or potassium carbonate, to form an intermediate bis-dinitro compound; and (2) reduction of the nitro-groups in a known manner, to form the diamine.

In a preferred embodiment, the diamine (II) employed is characterized by the positioning of the oxygen bridge at sites para- or meta- to the amine groups, especially the compounds

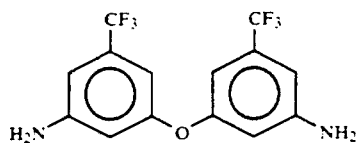

5,5'-oxy-bis[3-(trifluoromethyl)benzenamine] or

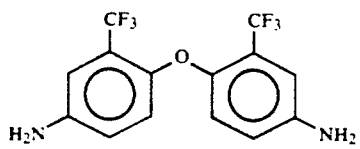

4,4'-oxy-bis[3-(trifluoromethyl)benzenamine]

In the preparation of the bis-imide, an aromatic diamine (II) is reacted with two equivalents of maleic anhydride or nadic anhydride. Typically, the reaction may be carried out by adding the anhydride to a solution of the diamine and heating the resulting mixture, with stirring, at a temperature of from about room temperature to about 180° Celsius until the reaction is substantially complete. Suitable solvents include, for example, dimethylacetamide, dimethylsulfoxide, N-methyl pyrrolidone, tetrahydrofuran, and the like.

The following examples are provided to further illustrate the invention in the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

Preparation of
4,4'-Oxy-bis[3-(trifluoromethyl)benzenamine]

4-Nitro-2-(trifluoromethyl)chlorobenzene (20.00 g, 88.7 mmol), 3-nitrobenzoic acid catalyst (0.0694 g, 0.0005 eq.) and sodium carbonate (4.62 g, 1.0 eq.) in dimethyl acetamide (30 mL) were stirred mechanically under a nitrogen atmosphere at 150° C. After 27 hours, gas chromatographic (GC) analysis showed that the conversion was 96.0% and the gas chromatographic analysis with internal standard (GC ISTD) yield of 4,4'-oxy-bis[3-(trifluoromethyl)nitrobenzene] was 86.4%. The reaction mixture was filtered to remove inorganic salts and the resulting filtrate was concentrated to give a red solid. Recrystallization from methanol gave 4,4'-oxy-bis[3-(trifluoromethyl)nitrobenzene] as beige solid (13.61 g, 81.2% yield, GC purity 99.9+%).

To a mixture of 4,4'-oxy-bis[3-(trifluoromethyl) nitrobenzene] (5.00 g, 12.6 mmol) and 10% palladium on carbon (0.11 g) in ethanol (100 mL), hydrazine hydrate (2.6 mL, 1.2 eq) Was added dropwise over 15 minutes. The reaction mixture was heated to a gentle reflux for 4 hours. After cooling, the catalyst was removed by filtration and the solvent removed under reduced pressure to give 4.00 g (94% yield) of the diamine 4,4'-oxy-bis[3-(trifluoromethyl)benzenamine] as a white solid (mp=126°-127° C.).

EXAMPLE 2

Preparation of
5,5'-Oxy-bis-(3-trifluoromethyl)benzenamine

To a 500 mL round bottom flask was charged 3,5-dinitrobenzotrifluoride (25.1 g), potassium fluoride (21.2 g), water (2.4 mL), and dimethylformamide (DMF, 125 mL). The reaction was heated to 160° C. for 24 hours. The reaction mixture was diluted with water (400 mL) and extracted with ether (3×150 mL). The ether was dried with magnesium sulfate and cooled to 5° C. and the resulting solid collected to give a total of 11.3 g (53.8% yield) of 5,5'-oxy-bis[3-(trifluoromethyl)-nitrobenzene].

To a mixture of 5,5'-oxy-bis[3-(trifluoromethyl) nitrobenzene] (4.00 g, 10.1 mmol) and 10% palladium on carbon (0.13 g) in ethanol (100 mL), hydrazine hydrate (2.1 mL, 1.2 eq) was added dropwise over 15 minutes while warming the reaction mixture at 45° C. Heating was continued for 2.25 additional hours. After cooling, the catalyst was removed by filtration and the solvent was removed under reduced pressure to give 3.31 g (98% yield) of the diamine 5,5'-oxy-bis[3-(trifluoromethyl)benzenamine] as a clear oil which solidified upon standing to give a white solid (mp=54°-55° C.).

EXAMPLE 3

Preparation of the Bismaleimide of
4,4'-Oxy-bis[3-(trifluoromethyl)benzenamine]

4,4'-Oxy-bis[3-(trifluoromethyl)benzenamine] (2.0 g, 0.006 mole) in anhydrous dimethylacetamide (2 mL) was added to a mixture of maleic anhydride (1.23 g, 1.05 eq), sodium acetate (0.88 g, 0.18 eq) and acetic anhydride (1.52 g, 2.5 eq). The mixture was stirred at room temperature for 45 minutes, then heated to 60° C. for 2 hours under a nitrogen atmosphere. The reaction mixture was diluted with water (20 mL) to obtain granular residue which was washed with water (2×50 mL) and dried to give a light brown solid (quantitative, mp=80° C.-100° C.). Analysis by gas chromatography showed the purity to be 100%. The structure was assigned by gas chromatography/mass spectroscopic analysis.

EXAMPLE 4

Preparation of the Bismaleimide of
4,4'-Oxy-bis[3-(trifluoromethvl)benzenamine]

The procedure of Example 3 was repeated except that in place of the dimethylacetamide there was substituted 2 mL of dimethyl sulfoxide.

EXAMPLE 5

Preparation of the Bismaleimide of
5,5'-Oxy-bis[3-(trifluoromethvl)benzenamine]

The procedure of Example 3 was repeated except that an equivalent amount of 5,5'-Oxy-bis[3-(trifluoromethyl)benzenamine] was substituted for the 4,4-isomer. The bismaleimide product had a melting point of 125°-130° C.

EXAMPLE 6

Preparation of the Bisnadimide of
4,4'-Oxy-bis[3-(trifluoromethvl)benzenamine]

4,4'-Oxy-bis[3-(trifluoromethyl)benzenamine] (2.0 g, 0.006 mole) and nadic anhydride (2.15 g, 1.10 eq) were heated in dimethyl acetamide (10 mL) at 160° C. for 3 hours. The reaction mixture was poured into water (30 mL). filtered, washed with water and dried to give the desired bisnadimide as a tan powder (quantitative. mp=218° C.-222° C.). Recrystallization from chloroform-methanol gave a light tan solid (mp=227.5° C.-229.0° C.). The structure was assigned by direct probe mass spectroscopic analysis. Gas chromatographic analysis using an injection port temperature of 250° C., caused the bisnadimide adduct to lose cyclopentadiene in a reverse Diels-Alder reaction to give the bismaleimide described in Example 3.

EXAMPLE 7

Preparation of the Bisnadimide of 5,5'-Oxy-bis[3-(trifluoromethyl)benzenamine]

The procedure of Example 6 was repeated except that an equal amount of 5,5'-Oxy-bis[3-(trifluoromethyl)benzenamine] was substituted for the 4,4'-isomer. Recrystallization of the bisnadimide product from chloroform-methanol gave a tan crystalline solid (mp=223.0° C.-224.5° C.). The structure was assigned by direct probe mass spectroscopic analysis.

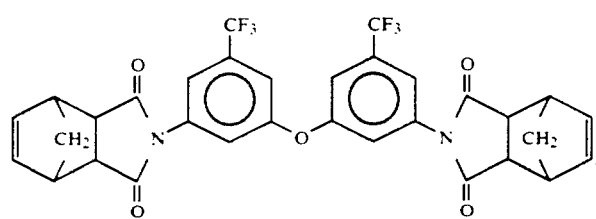

What is claimed is:

1. A bis-imide of the formula

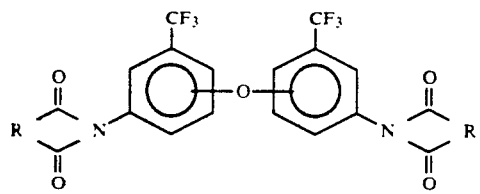

wherein R is a bivalent radical of the formula

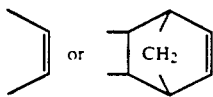

2. A bis-imide according to claim 1 of the formula

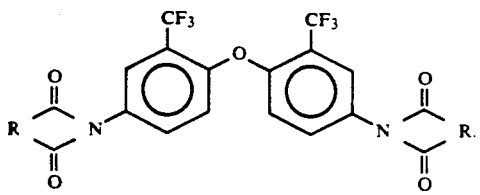

3. A bis-imide according to claim 1 of the formula

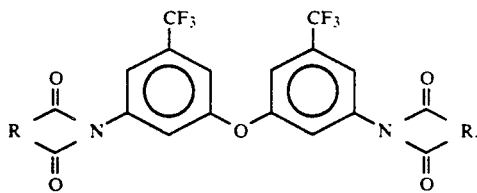

4. A bis-imide according to claim 1 wherein R is

5. A bis-imide according to claim 1 wherein R is

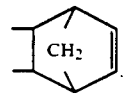

6. A bis-imide of the formula

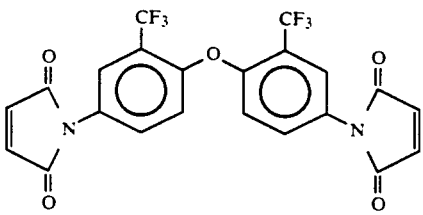

7. A bis-imide of the formula

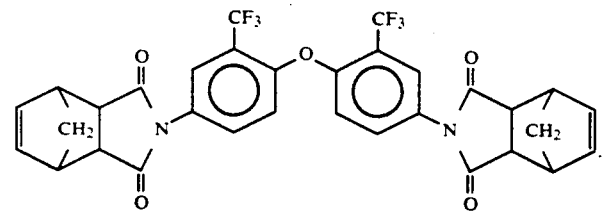

8. A bis-imide of the formula

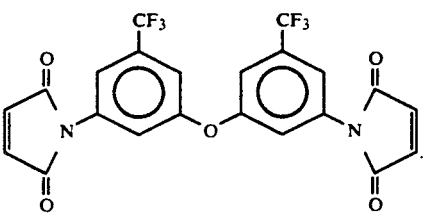

9. A bis-imide of the formula